United States Patent
Casto

[19]

[11] Patent Number: 6,126,696
[45] Date of Patent: Oct. 3, 2000

[54] FISHING ROD APPARATUS FOR UPPER EXTREMITY PROSTHESIS

[76] Inventor: Jack E. Casto, 901 Riviera Dr., Ponca City, Okla. 74601-3132

[21] Appl. No.: 09/062,779

[22] Filed: Apr. 20, 1998

Related U.S. Application Data

[60] Provisional application No. 60/047,407, May 22, 1997.

[51] Int. Cl.[7] ........................................... A61F 2/54
[52] U.S. Cl. ............................... 623/65; 43/21.2
[58] Field of Search ................... 623/65, 61, 57; 43/21.2; 224/922

[56] References Cited

U.S. PATENT DOCUMENTS

| | | |
|---|---|---|
| 1,344,357 | 6/1920 | Shirer . |
| 2,499,117 | 2/1950 | Smith ........................................ 224/259 |
| 3,036,312 | 5/1962 | Larsen et al. . |
| 3,490,078 | 1/1970 | Perez, Jr. . |
| 3,802,302 | 4/1974 | Bengston . |
| 4,661,113 | 4/1987 | Adkins . |
| 5,212,900 | 5/1993 | Perry ........................................ 43/21.2 |
| 5,464,444 | 11/1995 | Farquharson et al. . |

FOREIGN PATENT DOCUMENTS

| | | | |
|---|---|---|---|
| 5-7445 | 1/1993 | Japan .................. | 43/21.2 X |

Primary Examiner—David H. Willse
Attorney, Agent, or Firm—Richard C. Litman

[57] ABSTRACT

A fishing rod apparatus for use as an upper extremity prosthesis attachment. An upper extremity prosthesis receives the assembled components of the fishing rod apparatus, which comprises an operational extension of the upper extremity prosthesis. An adjustable wrist unit insertably engages an upper extremity prosthesis, and receives a modified handle member having a handle end and a reel seat end. The handle end has a threaded stud which engages the wrist unit. The reel seat end has a bore which receives a conventional rod blank by means of an extension adapted to fit the bore. The rod blank may be secured to the modified handle member by epoxy, or it may have means for releasably attaching to the modified handle member. Once the rod blank is secured in place, a conventional reel is mounted on the reel seat end of the modified handle member. The fishing rod apparatus of the present invention is most advantageously used by a fisherman who has lost only one arm. In use the rod is attached to the prosthesis, the fisherman's good arm being used to help guide the cast and manipulate the reel by grasping the modified handle member.

7 Claims, 3 Drawing Sheets

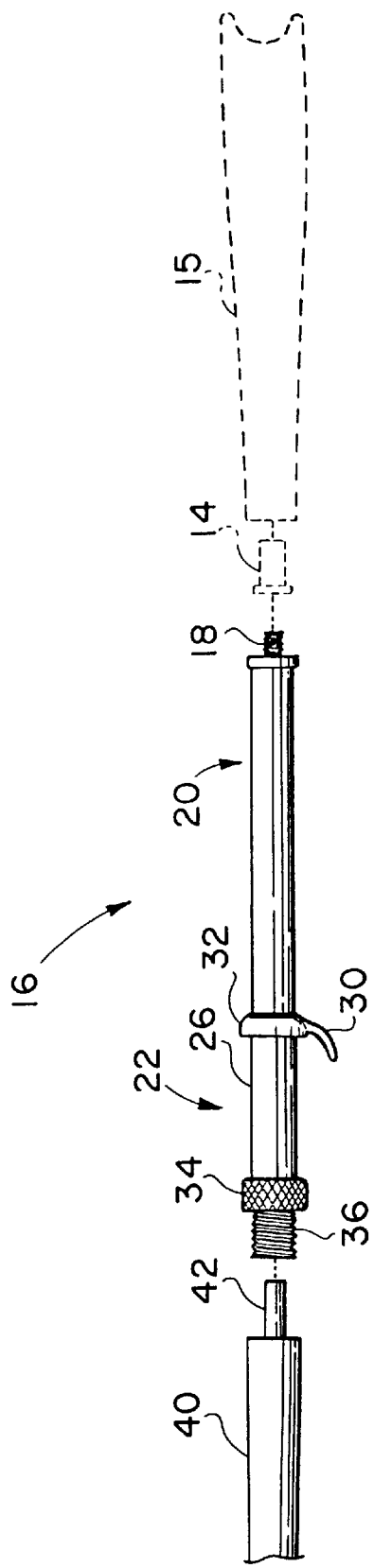

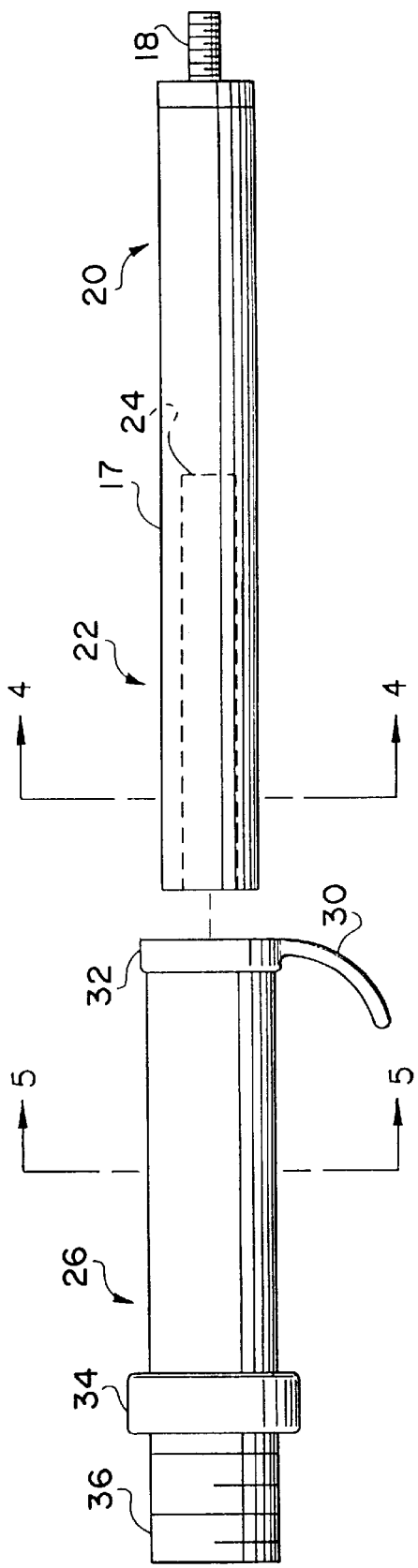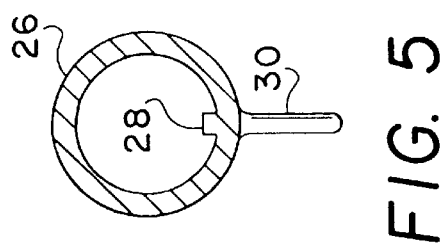

FISHING ROD APPARATUS FOR UPPER EXTREMITY PROSTHESIS

CROSS-REFERENCE TO RELATED APPLICATION

This application claims the benefit of U.S. Provisional Patent Application Serial No. 60/047,407, filed May 22, 1997.

BACKGROUND OF THE INVENTION

1. Field of the Invention

The present invention relates to upper extremity prostheses, and more specifically to a modular fishing rod apparatus for use with an upper extremity prosthesis.

2. Description of the Relevant Art

After the loss of a limb, upper extremity amputees often are fitted with a prosthesis with which to regain bilateral function and resume their daily activities. Many types of prostheses cosmetically or operationally emulate the hand, wrist, and/or arm itself. Some prostheses incorporate means for removably attaching an implement to the distal end thereof. Such devices eliminate the amputee's need to grasp and manipulate the implement with a prosthetic hand, as the implement comprises a continuous extension of the prosthesis.

U.S. Pat. No. 1,344,357 issued Jun. 22, 1920 to George A. Shirer teaches a cuff wrapped around the wrist having a slot and a stud on the side of the cuff. The cuff is used with implements such as knives and forks having shafts made of spring metal and having a slot defined in the shaft so that the shaft is inserted through the slot on the cuff, the slot on the shaft is fitted over the head of the stud on the cuff, and the shaft is pulled down to lock the implement in place.

Several inventions and patents have described different upper extremity implement attachment systems, many having a plurality of interchangeable tools. The tool-mounting prosthetic device of U.S. Pat. No. 3,490,078, for example, comprises a laceable sleeve having a solid forepiece for engaging a residual limb, where the forepiece has an inwardly-directed annular rim that receives a tubular threaded socket. The tubular threaded socket in turn receives a variety of tools, each having a threaded stud at the handle end for engaging the threaded socket. The prosthetic device of '078 concentrates exclusively on carpentry and cutting tools, such as hammers, screwdrivers, hatchets, machetes and handsaws.

Similarly, U.S Pat. No. 3,802,302 discloses a tool-holding prosthetic device. A set of specially-designed tools, including a hammer, wrenches and pliers, have handles with adapters that receive a snap connector having a spring loaded detent ball member, the snap connector threadably engaging a prosthetic arm. In an alternative, the connector may be a ball and socket connector so the tool may rotate or bend laterally to 90°.

The implement attachment of U.S. Pat. No. 4,661,113 features a connector with a ball and socket joint which is threadably attached to a prosthetic arm. The joint is secured by a crosspin through the ball to permit pivoting movement but precluding full rotational movement. A golf club, tennis racket, or other implement is threadably attached to the connector. Each of these implements is of the "swinging type," with the ball-socket joint of the body member enabling limited pivotal movement. Hence the attachment of '113 would not be well-suited for non-swinging type implements that instead require a steady and rigidly immobile extension, such as a fishing rod.

U.S. Pat. No. 3,036,312 discloses a fishing rod attachment especially for the fisherman with only one arm prosthesis. The attachment comprises a support arm that threads into the arm prosthesis, the support arm having a clamping block attached to its free end. The fisherman casts with his good arm and places the butt end of the rod in his mid-section while securing the rod in the clamping block, allowing him to operate the reel with his good hand.

Unlike in other artificial limb implement attachment devices, the rod used with the device of '312 is not itself an extension of the prosthesis. The musculature of the shoulder and residual limb are not used for any other purpose than holding the rod braced against the mid-section. Hence, the device fails to make full use of the residual functional capacity of the injured limb, and is uncomfortable in use from the necessity of supporting the rod with the mid-section of the body.

Other prosthesis tool attachment devices involve complex multi-component assemblies having a diverse multiplicity of attachable implements and providing articulation capabilities to allow a variety of positions relative to the prosthesis. U.S. Pat. No. 5,464,444, for example, teaches a two part attachment for an artificial arm, the first part threadably engaged to the artificial arm, the second part connected to the first part by a worm gear so that it pivots to various angles by manually operating the worm gear. Tools or implements attach to the second part by a spring loaded ball and detent connector. Among the claimed tools or implements are cutting tools, such as saws, files, knives, scrapers and awls, various wrenches, such as open and closed end wrenches, ratchet wrenches, adjustable wrenches, Allen wrenches and pipe wrenches, spoons, scoops, spatulas, brushes, fishing rods and stirring devices. While versatile, the device depends on a complicated and expensive mechanism and does not have features dedicated to the use of a fishing rod.

In light of the shortcomings of the above inventions and patents, there is a need for a fishing rod that is dedicated to an upper extremity prostheses. There is also a need for a fishing rod that comprises an operational extension of a person's residual limb to permit usage of residual upper extremity musculature for greater control and more versatile and natural bilateral motion. There is also a need for a prosthesis attachment apparatus that is easily handled by upper extremity amputees and serves the specific function of securing a fishing rod onto an upper extremity prosthesis.

None of the above inventions and patents, taken either singly or in combination, is seen to describe the instant invention as claimed.

SUMMARY OF THE INVENTION

Many upper extremity prosthesis implement attachment systems exist that incorporate a plurality of tools and other modular attachments. While versatile, these complex devices do not offer the simplicity and convenience of a prosthesis attachment having one exclusive use, often involving a leisure-related implement.

The present invention concerns a fishing rod apparatus for use as an upper extremity prosthesis attachment. The end of an existing upper extremity prosthesis, farthest from the amputee's residual limb, receives the assembled components of the fishing rod apparatus. The fishing rod apparatus of the present invention comprises an operational extension of the upper extremity prosthesis.

An adjustable wrist unit insertably engages an upper extremity prosthesis, and receives a modified handle member having a handle end and a reel seat end. The handle end has a threaded stud which engages the wrist unit. The reel seat end has a bore which receives a conventional rod blank by means of an extension adapted to fit the bore. The rod blank may be secured to the modified handle member by epoxy, or it may have means for releasably attaching to the modified handle member. Once the rod blank is secured in place, a conventional reel is mounted on the reel seat end of the modified handle member. Accordingly, it is a principal object of the invention to provide a fishing rod apparatus that allows an upper extremity amputee to easily and quickly assemble the components.

It is another object of the invention to permit an upper extremity amputee to utilize the residual upper extremity musculature for greater control and more versatile and natural bilateral motion while fishing.

It is a further object of the invention to produce a fishing rod prosthesis attachment that comprises an operational extension of an upper extremity prosthesis.

It is also an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2 is an exploded partial view of the components of a fishing rod according to the present invention.

FIG. 3 is an exploded view of the modified handle member according to the present invention.

FIG. 4 is a sectional view along the line 4—4 of FIG. 3.

FIG. 5 is a sectional view along the line 5—5 of FIG. 3.

Similar reference characters denote corresponding features consistently throughout the attached drawings.

DETAILED DESCRIPTION OF THE PREFERRED EMBODIMENT

Figure 1:
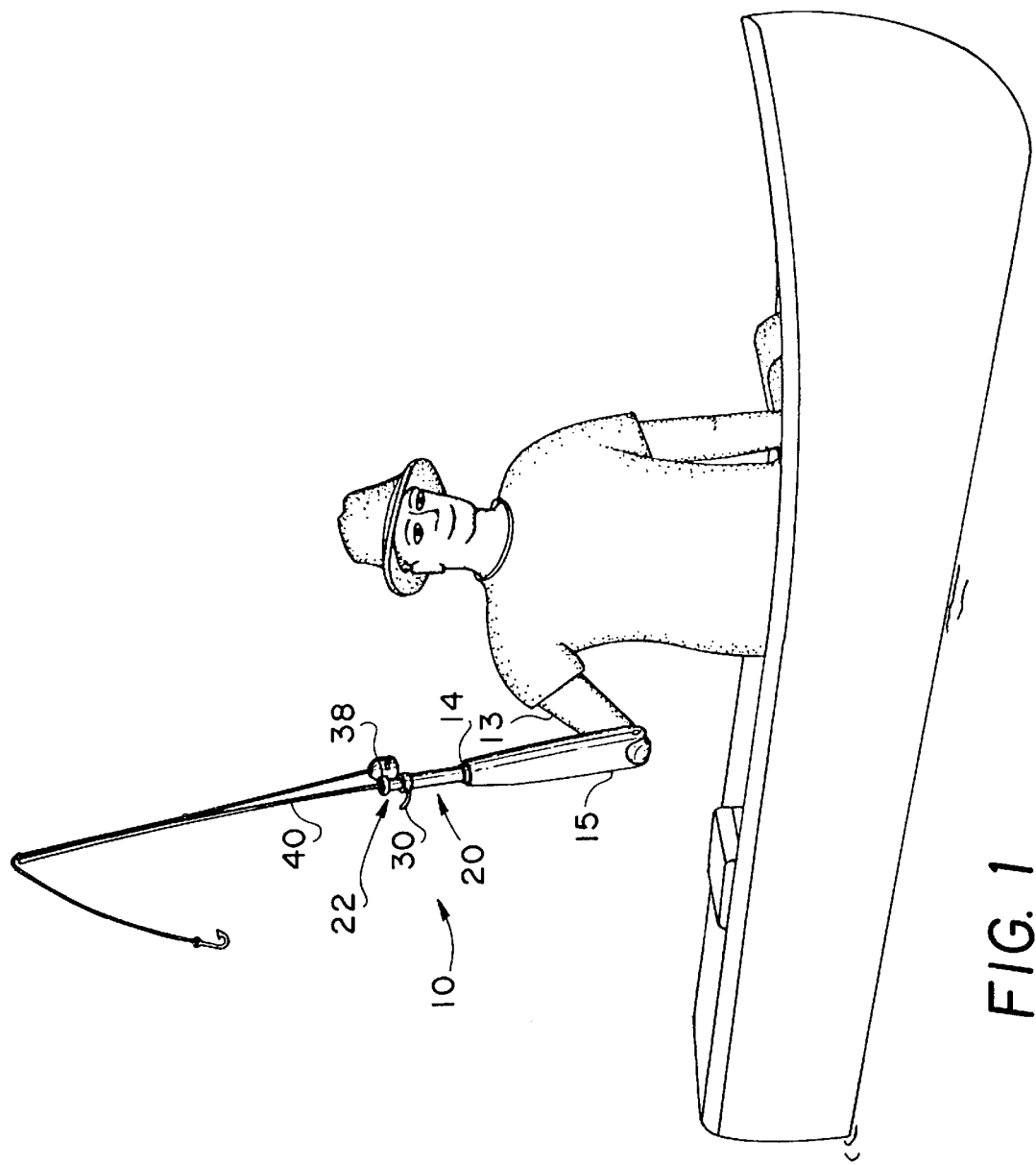
FIG. 1 is an environmental view of the present invention, as affixed to an upper extremity prosthesis.

The present invention, as referenced by 10 herein, is shown in use in FIG. 1. An existing upper extremity prosthesis 15 has an end farthest from the amputee's residual limb 13, which receives the assembled components of fishing rod apparatus 10. Fishing rod apparatus 10 comprises an operational extension of upper extremity prosthesis 15.

A conventional fishing rod consists generally of a handle, a rod blank, and a reel. The handle generally consists of a butt portion, a reel seat, and a grip. When fishing, the fisherman will cast his line by grasping the butt portion of the rod with one hand, perhaps wrapping his finger or fingers on a trigger grip or pistol grip, or using both hands with one hand on the grip portion of the handle. The amputee is unable to grip the butt with a hook or artificial hand and maintain a firm grasp. The amputee may be very desirous of using his amputated arm for casting, particularly if it was his dominant arm prior to amputation. The present invention uses a modified handle assembly threadably engaging a conventional wrist unit which snaps into the distal end of the prosthetic arm 15.

Now referring to FIG. 2, a standard adjustable wrist unit 14 conventional in the prosthetics industry is shown insertably engaging the distal end of upper extremity prosthesis 15, as known in the prior art. Wrist unit 14 has a threaded interior cavity, which receives a threaded stud 18 extending from the handle end 20 of a modified handle member 16.

The modified handle member 16 is best shown in FIG. 3. The modified handle member 16 consists of an adaptor 17 and a reel seat 26. The adaptor 17 is stock material which may be aluminum, titanium, steel or other malleable metal alloy having a cylindrical shape with a base approximately ⅞" in diameter and a total length of approximately 8 ¾". The modified handle member 16 and adaptor 17 have a handle end 20 and a reel seat end 22. The handle end 20 of the adaptor 17 has a threaded stud 18 adapted to fit conventional wrist unit 14 cut into the stock material, being substantially ⅜" in diameter and ¾" long with 24 bites per inch.

The reel seat end 22 of the adaptor 17 has a bore 24 defined longitudinally therein as shown in FIG. 4, and shown in broken lines in FIG. 3, adapted for receiving a rod blank 40. The bore 24 may be made by milling a ½" cavity approximately 4 inches deep into the adaptor 17 stock. The reel seat end 22 also has a groove 25 defined in the bottom surface of the adaptor 17. The adaptor 17 has a conventional reel seat 26 mounted on the reel seat end 22. The particular reel seat 26 shown in the Figures is a type of reel seat known in the industry as a trigger grip reel seat. The trigger grip reel seat 26 has a hollow cylinder which slides on to the reel seat end 22 of adaptor 17, the cylinder having a projection 28 on its inner surface as shown in FIG. 5 which engages the groove 25 so the reel seat 26 does not rotate on the adaptor 17.

The trigger grip reel seat 26 shown has a trigger projection 30, a reel brace 32, a lock nut 34, and a threaded portion 36. A reel 38 will typically be mounted on the top of the reel seat 26 between the reel brace 32 and the lock nut 34, the reel 38 having feet (not shown) which are secured by the locknut 34. When used in casting, the amputee may grasp the handle end 20 of the modified handle member 16 with his free hand, wrapping his index finger around trigger projection 30 to help support the rod and guide the cast.

It will be apparent that the present invention may have two embodiments. In one embodiment, the modified handle member 16 may be a single unit, with the adaptor 17 and the reel seat 26 being an integral unit. In the preferred embodiment, the modified handle member 16 consists of a conventional reel seat 26 which slides on the reel seat end 22 of adaptor 17 and is secured by epoxy or glue, the surface of the adaptor 17 having grooves defined therein to accommodate the epoxy.

As previously noted, a wide variety of conventional reel seats 26 are separately available from manufacturers, including trigger grip, pistol grip, straight grip, spinning reel, flying reel, etc. The present invention is not intended to be limited to a trigger grip reel seat. Some reel seats do not have a hollow cylinder throughout their entire length as the trigger grip reel seat does. In that event adaptor 17 may be provided as a bipartite unit, with the handle end 20 connected to one end of the reel seat 26 and the reel seat end 22 connected to the other end of the reel seat 26 unit.

The rod blank 40 of the present invention has a cylindrical extension 42 adapted for insertion into the bore 24 in the reel seat end 22 of adaptor 17. In the preferred embodiment, the extension 42 is similar to a dowel formed by filing or milling a shoulder around the circumference of the rod and the rod blank 40 is secured to the bore 24 of modified handle member 16 by epoxy or glue, the extension 42 having grooves defined on its surface to accommodate the epoxy. In alternative embodiments, the rod blank 40 and the adaptor 17 may have releasable means for attaching the rod blank 40, such as complementary external threading on extension 40 and internal threads in bore 24. The rod blank 40 may be made in a variety of lengths as are conventionally available, from a variety of materials such as plastic, fiberglass, titanium, graphite, aluminum, or composite, and has a plurality of line guides.

The reel seat 26 will accommodate any standard type of fishing reel, including spin cast, spinning, bait cast or fly fishing reels. The handle end 20 of the modified handle member 16 made be made from or encapsulated by a layer of rubber, plastic, cork, leather or composite material.

The dimension given for the length of the adaptor 17 stock, 8 ¾ inches, will result in a handle end 20 of approximately 3 inches in length, since the reel seat 26 and threaded stud 18 combined use 5 ¾ inches of the length of the adaptor 17. If a longer handle end 20 is desired, a longer piece of stock may be used in fabricating the adaptor. For example, stock lengths of 9 ¾ inches, 10 ¾ inches, and 11 ¾ inches, will result in handle end 20 lengths of approximately 4", 5", and 6" respectively.

In use, the fisherman threads the stud 18 into the wrist unit 14 and snaps the wrist unit 14 into the end of the prosthesis 15. The fisherman casts his rod 10, gripping the rod 10 at the handle end 20 of the modified handle member 16 with his good hand and wrapping his index finger around the trigger grip 30 to help support the rod 10 and guide the cast. After casting he may hold the rod 10 with his prosthetic arm 15, supporting the rod 10 by holding the handle end 20 with his good hand from time to time as his stump tires. The handle end 20 and grip 30 are also grasped with the good hand in order to use the thumb of his good hand to operate the reel 38 to lock the line or reel it in.

The fishing rod apparatus 10 of the present invention is most advantageously used by a fisherman who has lost only one arm. Depending on the reel seat 26, however, it may also find use with bilateral amputees.

It is to be understood that the present invention is not limited to the sole embodiment described above, but encompasses any and all embodiments within the scope of the following claims.

I claim:

1. A fishing rod apparatus for an upper extremity prosthesis for use with a fishing reel, comprising:

a) a fishing rod blank; and b) a modified handle member comprising an adaptor in combination with a reel seat, the adaptor having a handle end and a reel seat end, the reel seat being disposed on the reel seat end of said adaptor, the handle end having releasable means for engaging an upper extremity prosthesis and the reel seat end having rod engaging means for engaging said fishing rod blank, the reel seat having reel attaching means for attaching said fishing reel to the adaptor.

2. The fishing rod apparatus according to claim 1, wherein said releasable means comprises a threaded stud at the handle end of said adaptor, the stud being adapted for attachment to an internally threaded wrist unit, said wrist unit being adapted for engaging the distal end of said upper extremity prosthesis.

3. The fishing rod apparatus according to claim 2, wherein:

a) said rod engaging means comprises a bore defined longitudinally in the reel seat end of said adaptor; and b) said rod blank further comprises an extension adapted for insertion into the bore defined in said adaptor.

4. The fishing rod apparatus according to claim 3, wherein said rod blank is fixedly attached to said modified handle member by inserting the extension of said rod blank into the bore in said adaptor and securing the joint with epoxy.

5. An adaptor for securing a fishing rod blank and reel seat to an internally threaded wrist unit of an artificial arm, the adaptor comprising a cylindrical body having:

a) a handle end having releasable means for attachment to said wrist unit of said artificial arm;

b) a reel seat end, said reel seat end having rod engaging means for engaging said rod blank; and c) wherein said cylindrical body has a groove defined therein configured to receive a projection on said reel seat.

6. The adaptor according to claim 5, wherein said releasable means comprises a threaded stud at the handle end of said adaptor, the stud being adapted for attachment to said internally threaded wrist unit of said artificial arm.

7. The adaptor according to claim 6, wherein said rod engaging means comprises a bore defined longitudinally in the reel seat end of said adaptor, the bore being adapted for receiving said rod blank.

* * * * *